United States Patent [19]
Castillo

[11] Patent Number: 5,167,645
[45] Date of Patent: Dec. 1, 1992

[54] CHOLANGIOGRAPHY CATHETER INSERTER

[76] Inventor: R. Robert Castillo, 3000 Espanola, N.E., Albuquerque, N. Mex. 87110

[21] Appl. No.: 735,287

[22] Filed: Jul. 24, 1991

[51] Int. Cl.⁵ ............................................. A61M 5/32
[52] U.S. Cl. .................... 604/272; 604/158; 604/264
[58] Field of Search ............ 604/158, 159, 164, 264, 604/272

[56] References Cited

U.S. PATENT DOCUMENTS

| | | | |
|---|---|---|---|
| 4,650,472 | 3/1987 | Bates | 604/158 |
| 4,808,157 | 2/1989 | Coombs | 604/158 |
| 4,850,960 | 7/1989 | Grayzel | 604/158 |
| 4,958,901 | 9/1990 | Coombs | 604/158 |

FOREIGN PATENT DOCUMENTS

| | | | |
|---|---|---|---|
| 1810804 | 6/1970 | Fed. Rep. of Germany | 604/158 |
| 2305796 | 8/1974 | Fed. Rep. of Germany | 604/158 |
| 976993 | 11/1982 | U.S.S.R. | 604/158 |

OTHER PUBLICATIONS

"Laparoscopic Cholecystomy: Instrumentation and Technique" by E. Phillips, M. D., et al.; Journal of Laparoendoscopic Surgery vol. 1, No. 1 (1990) pp. 3-10.
Textbook: "Laparoscopic Cholangiography and Management of Choledocholithiasis" by Robert Bailey, M.D., et al.; Surgical Laparoscopy; Chapter 10 (1991); pp. 201-225.
"Cholangiogram"; Atlas of Endo Cholecystectomy with Auto Suture instruments by Karl A. Zucker, MD, FACS; (1990); p. 8.
"Arrow Balloon Cholangiography Catherization Sets"; Arrow International, Inc., Reading, Pa.
Cholangiocath Catheter, Model 908001; Surgimedics, Houston, Tex.
"Advanced Laparoscopic Instrumentation" by Marlow Surgical Technologies, Inc., Willoughby, Ohio; pp. 8-10.
"Laparoscopic Cholecystectomy"; Karl Storz—Endoskope; p. LCC7 Photocopy of American Catheter prototype.

Primary Examiner—Paul J. Hirsch

[57] ABSTRACT

The disclosure is directed to a cholangiography catheter insertion tool, or introducer. In the preferred embodiment, the tool comprises a hollow cylinder with an ovate directional aperture lying in the plane of a tangent to the cylinder and parallel to the longitudinal axis of the cylinder. Also disclosed is a method of using the tool.

26 Claims, 3 Drawing Sheets

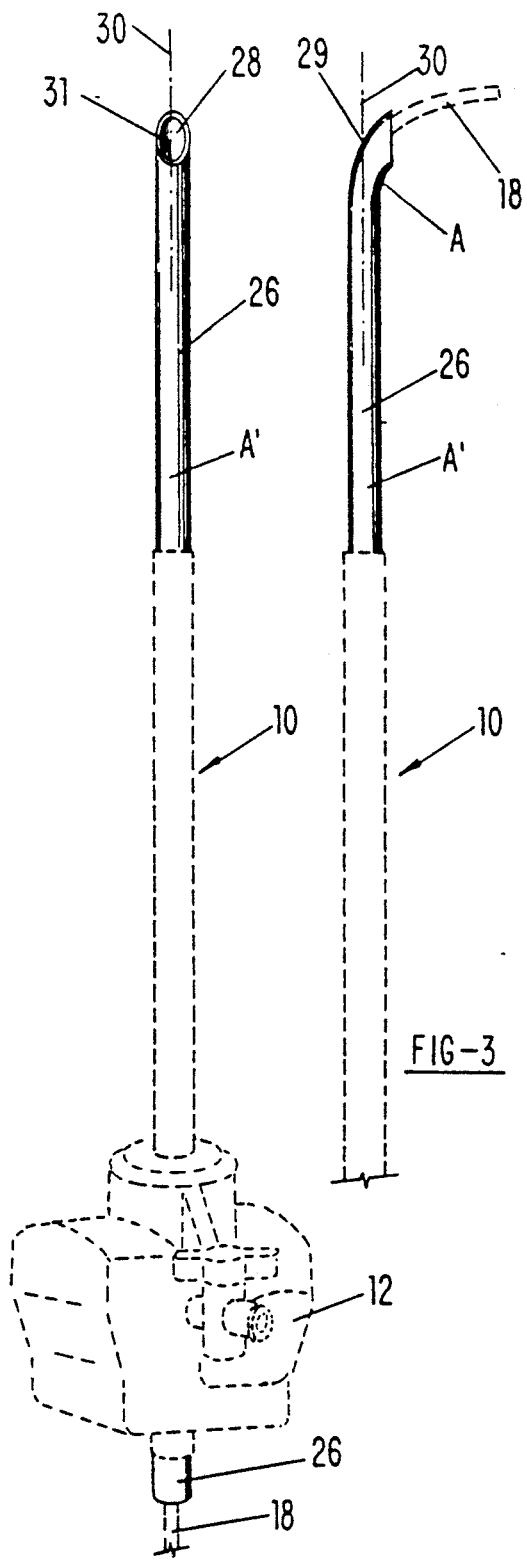
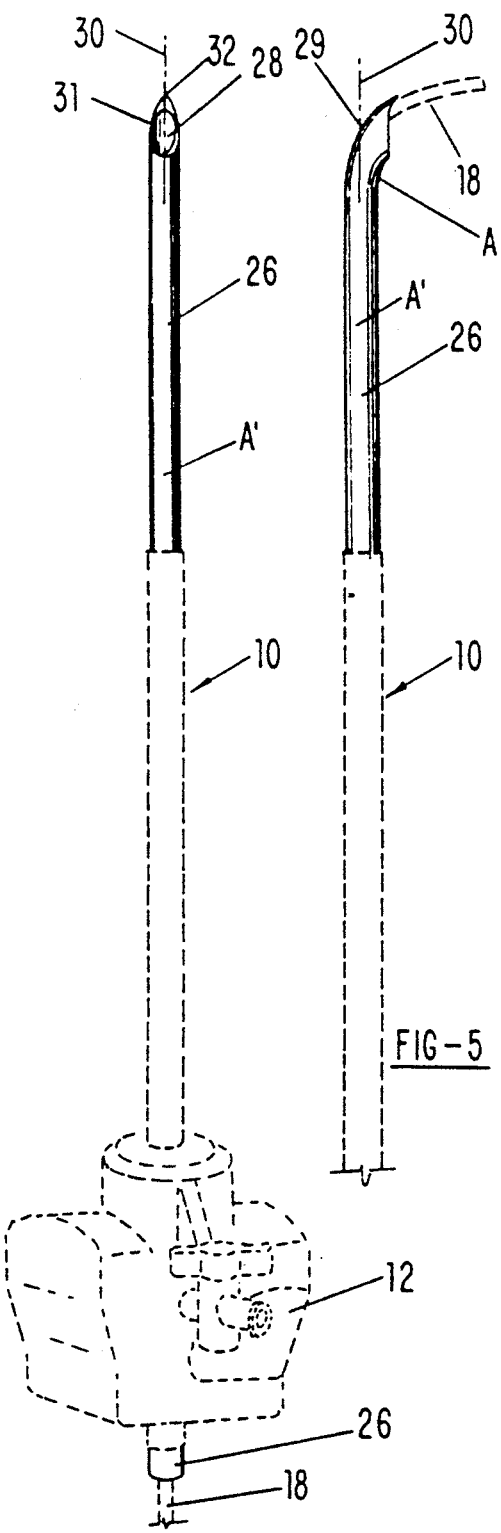

CHOLANGIOGRAPHY CATHETER INSERTER

BACKGROUND OF THE INVENTION

1. Field of the Invention (Technical Field)

The present invention relates to a cholangiography catheter introducer article, and a method for its use.

2. Background Art

Increasingly, less invasive surgical procedures are supplanting the open surgical procedures of the past. In no area is this more apparent than in surgical removal of the gallbladder, or cholecystectomy, for cholecystitis (inflammation of the gallbladder or biliary ducts) or cholelithiasis (stones) of the gallbladder or biliary ducts. Laparoscopic (endoscopic insertion into the peritoneal cavity) cholescystectomy and its resultant decreases in morbidity, hospital stay, and recuperative time favor increased acceptance of this procedure by the surgical community.

Further, many, if not most surgeons versed in the laparoscopic procedure, prefer conducting cholangiography to define the ductal anatomy and identify common duct stones prior to transsection of anatomy. In this subprocedure, a transverse incision is made in the cystic duct. A cholangiography catheter led through an intraperitoneal trocar is passed through the incision into the cystic duct and subsequently into the common duct.

Cannulation of the cystic duct by the cholangiography catheter is often a difficult and tricky process. The catheter must first traverse an approximate right angle through the incision into the cystic duct, and a further approximate right angle bend into the common duct. The prior art has employed catheters of "memory" plastic with curved insertion portions. Alternatively, guidewires inside catheters have been used to properly cannulate the cystic and common bile ducts. Graspers, specially designed cholangiography guides, and conventional suction-irrigation cannulae have been used.

Needless to say, manipulation of catheters through trocars is difficult at best, and may occupy two or more surgical personnel.

SUMMARY OF THE INVENTION

Disclosure of the Invention

The present invention relates to a tool for inserting a catheter into a duct, the tool comprising an elongated tube having a longitudinal axis and telescopically positionable within a trocar. The elongated tube further comprises a curved distal end and an aperture disposed at said distal end. A catheter extends through the trocar, said elongated tube, and said aperture.

In the preferred embodiment, the aperture extends in a plane parallel to the longitudinal axis of said elongated tube and the aperture comprises an ovate aperture extending in a plane tangent to said elongated tube or ovate aperture at a range of angles 45° on either side relative to the tangent to the cylinder of said elongated tube.

The elongated tube and/or distal end may comprise an aluminum material, a stainless steel material, a thermoplastic or thermosetting plastic material, such as polypropylene material, or the like. The elongated tube preferably comprises a length in the range of between approximately 25 and 35 cm.

In alternative embodiments, the distal end may comprise a sharpened portion or a lanceolate portion. The distal end may comprise a removably attachable tip positionable on a rod which is telescopically positionable within the trocar. The distal end may comprise a notched flexible tube, curved and joined at said notches, or at least two joined units forming said curve.

The invention further relates to a method of performing cholangiography comprising the steps of making a transverse incision in a cystic duct; inserting a cholangiography catheter inserter into the incision; and inserting a cholangiography catheter through the inserter and into the cystic duct. The cholangiography catheter inserter preferably comprises an ovate aperture. The cholangiography catheter inserter may further comprise a distal end with a sharpened or lanceolate portion.

An object of the present invention is the provision of a cholangiography catheter insertion tool which is simple to use and directionally effective.

Yet another object of the present invention is the provision of a cholangiography catheter inserter tool which is easy and inexpensive to manufacture.

An advantage of the present invention is that it may be used with existing surgical tools.

Yet another advantage of the present invention is that it be fabricated of disposable materials.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention.

FIG. 2 is the preferred cholangiography catheter introducer of the invention;

FIG. 3 is the FIG. 2 embodiment of the invention rotated 90° to the right;

FIG. 4 is an alternative embodiment of cholangiography catheter introducer of the invention;

FIG. 5 is the FIG. 4 embodiment of the invention rotated 90° to the right;

DESCRIPTION OF THE PREFERRED EMBODIMENTS

Best Modes for Carrying Out the Invention

Figure 1:
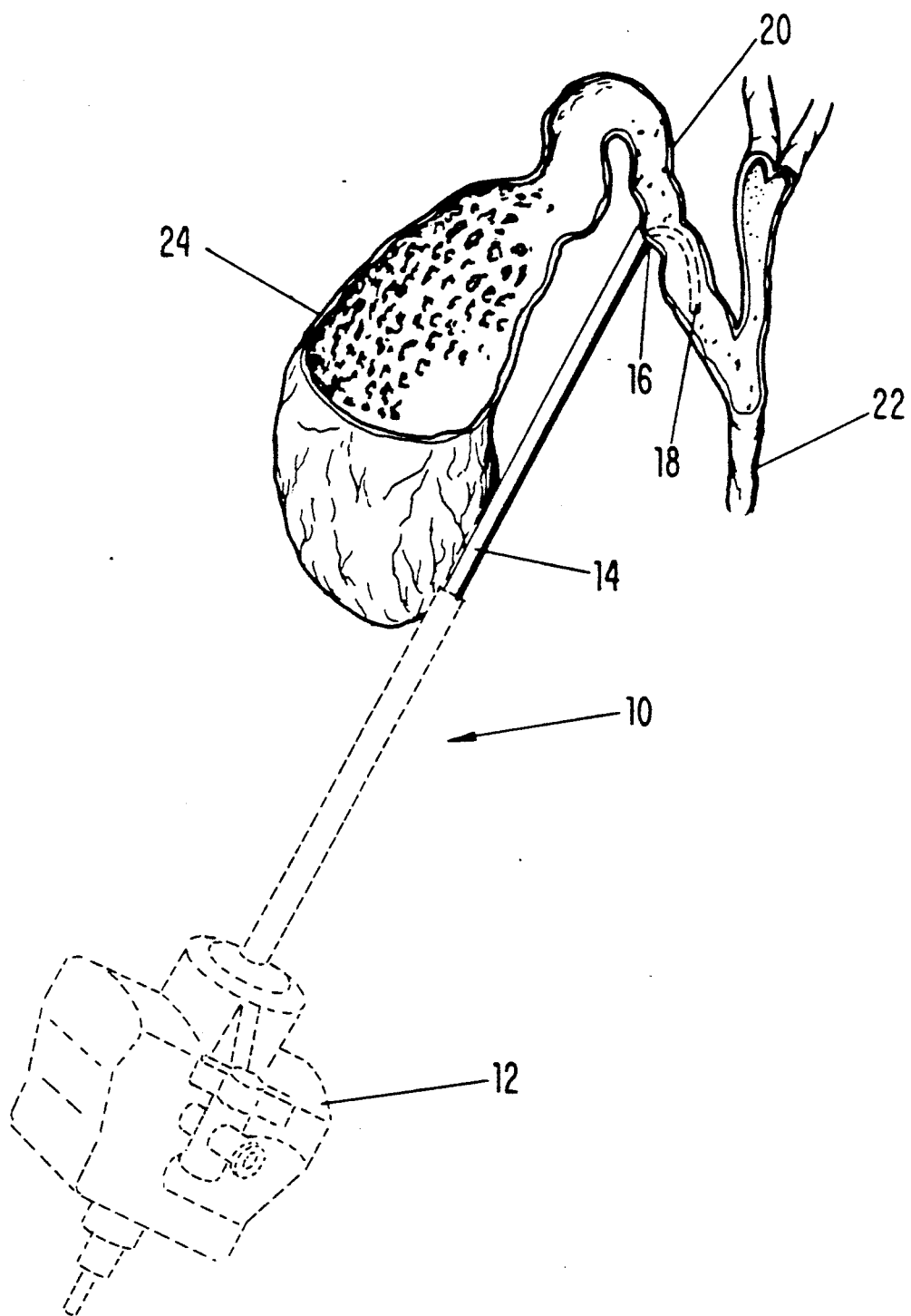
FIG. 1 is a cutaway and phantom view of a prior art trocar, cannula, and catheter inserted into a cystic duct.

FIG. 1, illustrating the prior art, shows trocar 10 in phantom as it might be inserted into the peritoneal cavity 24 prior to cholescystectomy. Trocar 10, usually of 5 or 10 mm diameter, is a cylinder comprising valve 12 for initiating and maintaining insufflation and permitting desufflation of $CO_2$ constituting the pneumoperitoneum. Ordinary suction-irrigation tool 14, comprising openings at both ends, is shown inserted in trocar 10. Suction-irrigation tool 14 is further depicted inserted into transverse incision 16 in cystic duct 20. Endoscopic catheter 18 is depicted as inserted in cystic duct 20 prior to commencement of cholangiography.

The insertion or introduction of catheter 18 into cystic duct 20, and ultimately into common bile duct 22 is, at best, a difficult and awkward maneuver. First, transverse incision 16 is made in cystic duct 20, usually with microscissors. Following the incision, suction-irrigation tool 14, having been passed through trocar 10, is inserted through incision 16. This insertion may be attended with difficulty due to an undersized or misplaced incision. Catheter 18 is then manipulated (sometimes by two or more surgical personnel) through suction-irrigation tool 14 into cystic duct 20. Catheter 18 must be sufficiently small and of the proper stiffness to negotiate the angular entrance required. Subsequent bending and manipulation is also required for entrance of catheter 18 into common bile duct 22.

FIGS. 2 and 3 depict the preferred cholangiography catheter introducer 26 of the invention. Tool 26 is generally 5 mm in diameter, corresponding to the smallest sized trocar with which it is to be used. In the event trocar 10 is of great internal diameter relative to the diameter of introducer tool 26, gaskets and other gas sealing means, as are well known in the art, may be used to prevent gas leakage and assure integrity of the pneumoperitoneum.

The introducer tool 26 of the invention comprises a cylinder which further comprises a hollow lumen. Tool 26 comprises a length in the range of between approximately 25 and 35 cm.

Distal end 31 of introducer tool 26 comprises ovate aperture 28 in communication with the lumen of the tool. The plane of aperture 28 may coincide with the plane tangent to the cylinder of tool 26, but may also lie 45° on either side of the plane. Ovate aperture 28 is created by bending tool 26 90° and serving the bend at the tangent plane. Spoon-like ovate aperture 28 and corresponding curve 29 thus form and serve as directional guides for proper catheter placement in the cystic duct 20.

As is apparent in FIGS. 2 and 3, the plane of ovate aperture 28 is preferably parallel to the longitudinal axis 30 of introducer tool 26. As is further apparent in FIGS. 2, 3, 5, 6, and 8, distal tip 31 may project substantially beyond a plane A—A' tangent to the outside surface of the cylinder of tool 26. Further, a line normal to the plane of ovate aperture and passing through its center would also be normal to longitudinal axis 30. However, ovate aperture distal tip 31 of introducer tool 26 may further comprise a sharpened or lanceolate tip 32, as depicted in FIGS. 4 and 5. Such a tip facilitates entrance into transverse incision 16, especially when such incision is of insufficient width.

Figure 6:
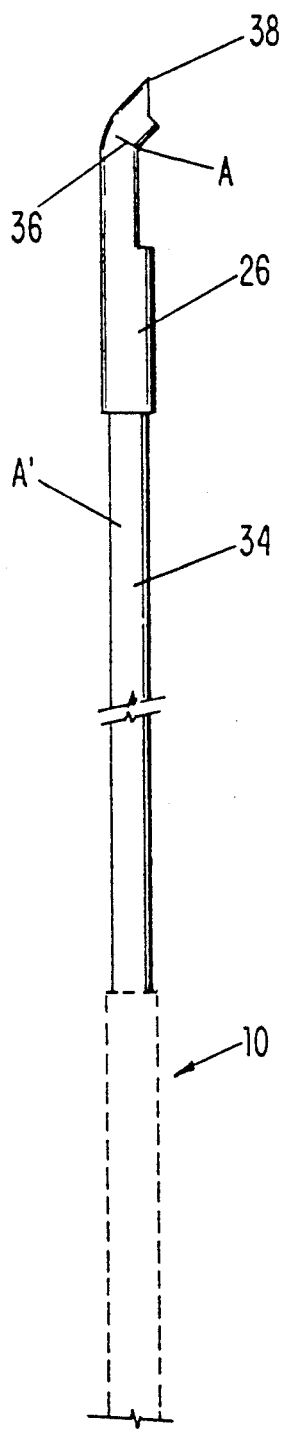
FIG. 6 is a side view of an alternative tip embodiment of the invention.
Figure 7:
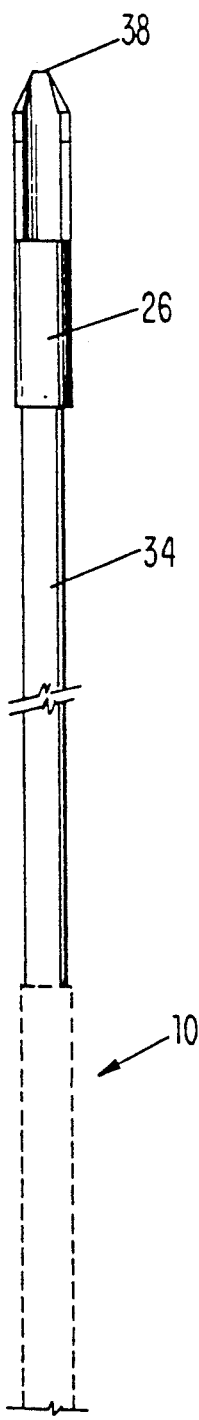
FIG. 7 is a front view of the FIG. 6 embodiment.

FIGS. 6 and 7 illustrate an alternative embodiment of the invention in which the introducer tool 26 comprises a removably attachable tip on rod 34, which rod 34 then fits within trocar 10. As can be appreciated by those skilled in the art, all of the embodiments shown in the drawings and those encompassed by the present invention could be either tips on a rod or integral with the rod. The embodiment of FIGS. 6 and 7 is preferably made of a flexible plastic material which can be cut to form two side notches 36 allowing the end to be curved over with the notches glued or otherwise joined together. A pointed tip 38 is useful for entry into traverse incision 16.

Figure 8:
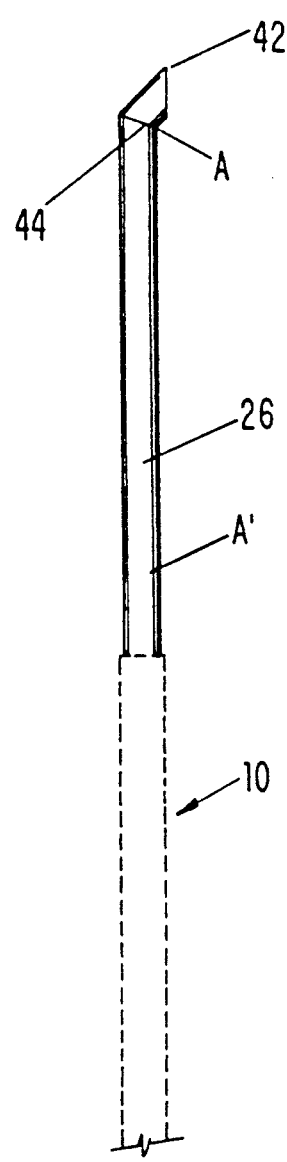
FIG. 8 is an alternative multiple end piece embodiment of the invention.
Figure 9:
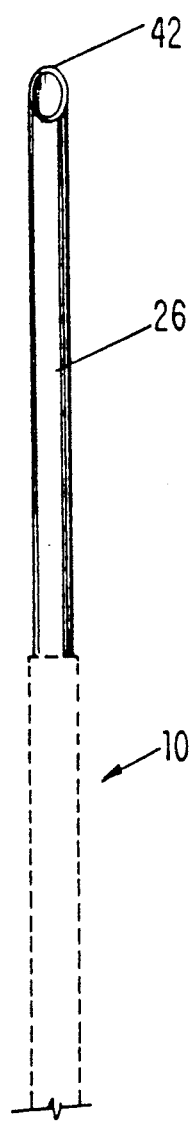
FIG. 9 is a front view of the FIG. 8 embodiment.

FIGS. 8 and 9 illustrate yet another alternative embodiment of tool introducer 26 in which two distal end pieces 40 and 42 are glued or otherwise joined together at juncture 44 to allow for a curved distal end. As can be appreciated by those skilled in the art, many types of junctures and shapes are possible with this multiple piece embodiment.

Introducer tool 26 may comprise several materials. Stainless steel and aluminum provide strength. On the other hand, since cholangiography normally requires removal of all unnecessary metal instruments from the field, the various plastics, generally including the thermoplastic and thermosetting plastics, are particularly suitable. Polypropylene is a preferred material which is approved by the Food and Drug Administration (FDA). The use of plastic introducer tools, which are disposable, further lessens the risk of infection, both to the patient and others. Other suitable materials will suggest themselves to those ordinarily skilled in the art.

Further, other uses and modifications of introducer tool 26 will suggest themselves to those ordinarily skilled in the art. For example, introducer tool 26 may be used in other surgical applications requiring catheter insertion, such as arterial or urethral catheterization. A variety of catheters may be used therewith, including balloon catheters.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

What is claimed is:

1. A tool for inserting a catheter into a duct comprising:
   elongated substantially straight tubular means having no more than a single lumen, a longitudinal axis and telescopically positionable within trocar means;
   said elongated tubular means further comprising a curved distal end and ovate aperture means disposed at said distal end;
   said curved distal end and said aperture means comprising discrete tip means extending substantially beyond a plane tangent to an outside surface of said elongated tubular means, said plane being parallel to said longitudinal axis;
   means for receiving a catheter extending through said trocar means, said elongated tubular means, and said aperture means; and
   wherein said tip means directs said catheter into an anatomical lumen.

2. The invention of claim 1 wherein the plane of ovate aperture means extends at a range of angles 45° on either side relative to the tangent to the cylinder of said elongated tubular means.

3. The invention of claim 1 wherein said elongated tubular means comprises an aluminum material.

4. The invention of claim 1 wherein said elongated tubular means comprises a stainless steel material.

5. The invention of claim 1 wherein said elongated tubular means comprises a material selected from the group consisting of thermoplastic plastics and thermosetting plastics.

6. The invention of claim 5 wherein said elongated tubular means comprises a polypropylene material.

7. The invention of claim 1 wherein said elongated tubular means comprises a length in the range of between approximately 25 and 35 cm.

8. The invention of claim 1 wherein said distal end comprises a lanceolate portion.

9. The invention of claim 1 wherein said elongated tubular means comprises a removably attachable tip positionable on a rod which is telescopically positionable within the trocar.

10. The invention of claim 1 wherein said curved distal end comprises a notched flexible tube, curved and joined at said notches.

11. The invention of claim 1 wherein said curved distal end comprises at least two joined units forming said curve.

12. A cholangiography catheter inserter comprising:
hollow cylinder means having no more than a single lumen, a longitudinal axis and comprising a proximal and distal end;
said distal end comprising a curve and an ovate aperture; and
said distal end extending beyond a plane tangent to an outside surface of said hollow cylinder means, said plane being parallel to said longitudinal axis.

13. The invention of claim 12 wherein said hollow cylinder means comprises an aluminum material.

14. The invention of claim 12 wherein said hollow cylinder means comprises a stainless steel material.

15. The invention of claim 12 wherein said hollow cylinder means comprises a material selected from the group consisting of thermoplastic plastics and thermosetting plastics.

16. The invention of claim 12 wherein said hollow cylinder means comprises a polypropylene material.

17. The invention of claim 12 wherein said hollow cylinder means comprises a length in the range of between approximately 25 and 35 cm.

18. The invention of claim 12 wherein said distal end comprises a sharpened portion.

19. The invention of claim 12 wherein said distal end comprises a lanceolate portion.

20. The invention of claim 12 wherein the plane of the ovate aperture extends at a range of angle 45° on either side relation to the tangent to said cylinder.

21. The invention of claim 12 wherein said distal end comprises a notched flexible cylinder, curved and joined at said notches.

22. The invention of claim 12 wherein said distal end comprises at least two joined units forming said curve.

23. A method of performing cholangiography comprising the steps of:
a) making a transverse incision in a cystic duct;
b) placing a single lumen cholangiography catheter inserter with a discrete extended tip into or adjacent to the incision;
c) inserting a cholangiography catheter through the inserter; and
d) directing the catheter into the cystic duct by means of the discrete extended tip on the inserter.

24. The method of claim 23 wherein the step of placing the cholangiography catheter inserter comprises the step of placing a cholangiography catheter inserter with an ovate structure into or adjacent to the incision.

25. The method of claim 23 wherein the step of inserting the cholangiography catheter comprises the step of inserting a lanceolate portion of the cholangiography catheter.

26. The method of claim 23 wherein the step of inserting the cholangiography catheter comprises the step of inserting a sharpened portion of the cholangiography catheter.

* * * * *